United States Patent
Chou et al.

(10) Patent No.: US 11,439,730 B2
(45) Date of Patent: Sep. 13, 2022

(54) CELL SHEET CONSTRUCT FOR NEUROVASCULAR RECONSTRUCTION AND MANUFACTURE THEREOF

(71) Applicant: NATIONAL DEFENSE MEDICAL CENTER, Taipei (TW)

(72) Inventors: Chung-Hsing Chou, Taipei (TW); Dueng-Yuan Hueng, Taipei (TW); Tsung-Neng Tsai, Taipei (TW)

(73) Assignee: NATIONAL DEFENSE MEDICAL CENTER, Taipei (TW)

( * ) Notice: Subject to any disclaimer, the term of this patent is extended or adjusted under 35 U.S.C. 154(b) by 374 days.

(21) Appl. No.: 16/705,314

(22) Filed: Dec. 6, 2019

(65) Prior Publication Data
US 2020/0108176 A1   Apr. 9, 2020

Related U.S. Application Data

(62) Division of application No. 14/826,927, filed on Aug. 14, 2015, now Pat. No. 10,537,664.

(30) Foreign Application Priority Data

Aug. 15, 2014   (TW) .................................. 103128059

(51) Int. Cl.
*A61L 27/38*   (2006.01)
*A61L 27/36*   (2006.01)
(Continued)

(52) U.S. Cl.
CPC .......... *A61L 27/3891* (2013.01); *A61K 35/30* (2013.01); *A61K 35/44* (2013.01);
(Continued)

(58) Field of Classification Search
CPC .. A61L 27/3891; A61L 27/24; A61L 27/3633; A61L 27/3675; A61L 27/3808;
(Continued)

(56) References Cited

U.S. PATENT DOCUMENTS

2006/0153815 A1   7/2006 Seyda et al.

OTHER PUBLICATIONS

Hicks et al. In Vivo and In Vitro Characterization of the Angiogenic Effect of CTX0E03 Human Neural Stem Cells. Cell Transplantation (2013), v22, p. 1541-1552; (Year: 2013).*
(Continued)

*Primary Examiner* — Sean C. Barron
(74) *Attorney, Agent, or Firm* — Locke Lord LLP; Tim Tingkang Xia, Esq.

(57) ABSTRACT

The invention relates to a cell sheet construct for neurovascular reconstruction. The cell sheet construct has a vascular endothelial cell layer and a neural stem cell layer, and the two layers are physically in direct contact with each other, where the vascular endothelial cell layer forms branching vasculatures, and the neural stem cell layer differentiates into neurons. The invention also relates to a method for manufacturing the cell sheet construct, having the following steps: culturing vascular endothelial cells on a substrate to form a vascular endothelial cell layer, seeding neural stem cells on the vascular endothelial cell layer to make the neural stem cells be physically in direct contact with the vascular endothelial cell layer, and culturing the neural stem cells and the vascular endothelial cell layer to differentiate into neurons and branching vasculatures to form a cell sheet construct.

8 Claims, 7 Drawing Sheets

(51) Int. Cl.
  *A61L 27/24* (2006.01)
  *C12N 5/071* (2010.01)
  *A61K 35/30* (2015.01)
  *C12N 5/079* (2010.01)
  *A61K 35/44* (2015.01)

(52) U.S. Cl.
  CPC ........... *A61L 27/24* (2013.01); *A61L 27/3633* (2013.01); *A61L 27/3675* (2013.01); *A61L 27/383* (2013.01); *A61L 27/3808* (2013.01); *A61L 27/3878* (2013.01); *C12N 5/0618* (2013.01); *C12N 5/0697* (2013.01); *A61L 2430/32* (2013.01); *C12N 2500/25* (2013.01); *C12N 2500/46* (2013.01); *C12N 2501/11* (2013.01); *C12N 2501/115* (2013.01); *C12N 2501/392* (2013.01); *C12N 2502/088* (2013.01); *C12N 2502/28* (2013.01); *C12N 2533/54* (2013.01)

(58) Field of Classification Search
  CPC ............... A61L 27/383; A61L 27/3878; A61L 2430/32; A61K 35/30; A61K 35/44; C12N 5/0618; C12N 5/0697; C12N 2500/25
  See application file for complete search history.

(56) References Cited

OTHER PUBLICATIONS

Kwon et al. Rapid cell sheet detachment from Poly(N-isopropylacrylamide)-grafted porous cell culture membranes. J Biomed Mater Res (2000), 50, 82-89. (Year: 2000).*

Kushida et al. Two-dimensional manipulation of differentiated Madin-Darby canine kidney (MDCK) cell sheets: The noninvasive harvest from temperature-responsive culture dishes and transfer to other surfacesJournal of Biomedical Materials Research (2001), 54, 37-46. (Year: 2001).*

Donato et al. Differential development of neuronal physiological responsiveness in two human neural stem cell lines. BMC Neuroscience (2007), v8(36), 11 pages. (Year: 2007).*

Diaz-Coranguez et al. Transmigration of Neural Stem Cells across the Blood Brain Barrier Induced by Glioma CellsPLOS One (2013), 8(4), e60655, 13 pages. (Year: 2013).*

Eppendorf TDS 48-well plates (2013). Retrieved from: https://www.eppendorf.com/product-media/doc/en/90686/Eppendorf_Consumables_Technical-data_Cell-Culture-Plate-48-Well.pdf (Year: 2013).*

Galli et al. The neurosphere assay applied to neural stem cells and cancer stem cells. Methods Mol Biol (2013);986:267-77. (Year: 2013).*

Roitbak T. et al., Neural Stem/Progenitor Cells Promote Endothelial Cell Morphogenesis and Protect Endotheial Cells against Ischemia via HIF-1a-regulated VEGF Signaling, J. of Cereb. Blood Flow & Metab., 2008, 28, 1530-1542.

Zhang XM et al., Dose-dependent effect of vascular endotheial cells on the in vitro directional differentiation of neural stem cells into neurons, J. of Clin. Rehab. Tissue Eng. Res., 2007, 11(24), 4670-4673.

Liu Ai-qun et al., Effect of LN and CMECs on Differentiation of NSCs, J. of Univ. of S. China (Med Ed.), 2009; 37(1): 14-17.

Ali Jahanbazi Jahan-Abad et al., Human Neural Stem/Progenitor Cells Derived from Epileptic Human Brain in a Self-Assembling peptide Nanoscaffold Improve Traumatic brain Injury in Rats, Molecular Neurobiology, 2018, Springer.

* cited by examiner

CELL SHEET CONSTRUCT FOR NEUROVASCULAR RECONSTRUCTION AND MANUFACTURE THEREOF

CROSS-REFERENCE TO RELATED APPLICATIONS

This application is a Divisional of U.S. application Ser. No. 14/826,927, filed on Aug. 14, 2015, and claims priority under 35 U.S.C. § 119(a) on Patent Application No. 103128059 filed in Taiwan, R.O.C. on Aug. 15, 2014, the entire contents of which are hereby incorporated by reference.

Some references, if any, which may include patents, patent applications and various publications, may be cited and discussed in the description of this invention.

The citation and/or discussion of such references, if any, is provided merely to clarify the description of the present invention and is not an admission that any such reference is "prior art" to the invention described herein. All references listed, cited and/or discussed in this specification are incorporated herein by reference in their entireties and to the same extent as if each reference was individually incorporated by reference.

BACKGROUND OF THE INVENTION

1. Field of the Invention

The invention relates to a cell sheet construct for neurovascular reconstruction, particularly to a cell sheet construct that is formed by co-culturing vascular endothelial cells with neural stem cells being physically in direct contact with each other to differentiate into branching vasculatures and neurons of the cell sheet construct.

2. Description of the Related Art

Cell-based therapies have been emerging as a promising therapeutic strategy for treating damaged or diseased organs and tissues. However, when being applied to the highly complicated nervous system, such as stroked brains, cell-based therapies remain to be improved further. In order to restore function of the damaged central nervous system by cell-based therapies, neurons have to be located in an appropriate microenvironment in the brain to transmit neural signals. Since neurons, which transmit neural signals, are regulated by vascular endothelial cells and interact with each other, neurons have to be situated in the neurovascular unit (NVU) to function appropriately.

Some researchers tried to create regenerated neurovascular tissue in vitro by the methods of tissue engineering. However, these teams were unable to create cell sheet having neurovascular tissues by co-culturing neural stem cells and vascular endothelial cells [Hicks C, Stevanato L, Stroemer R P, Tang E, Richardson S, Sinden J. In vivo and in vitro characterization of the angiogenic effect of CTX0E03 human neural stem cells. Cell transplantation. 2013; 22:1541-1552]. The main difficulty of these researches is that the suitable conditions for differentiation of neural stem cells and vascular endothelial cells are different. For example, Hicks et al. used Matrigel as the substrate for vascular endothelial cells to form branching vasculature tissues, but it was unable to provide neural stem cells an appropriate microenvironment to differentiate into neurons. In addition, because Matrigel is a mixture, Matrigel from different manufactures and different batches has different ingredients, which cannot provide a consistent condition to induce differentiation of neural stem cells.

Therefore, it is necessary to develop the techniques of constructing the neurovascular tissue, a cell sheet of neural stem cells-vascular endothelial cells (NSC-EC) having differentiated neurons and branching vasculatures, in order to promote neurovascular reconstruction.

SUMMARY OF THE INVENTION

One aspect of the present invention provides a cell sheet construct for neurovascular reconstruction, comprising a vascular endothelial cell layer and a neural stem cell layer. The vascular endothelial cell layer has vascular endothelial cells, and the neural stem cell layer has neural stem cells. The vascular endothelial cell layer is physically in direct contact with the neural stem cell layer, the vascular endothelial cell layer differentiates into branching vasculatures, and the neural stem cell layer differentiates into neurons.

Another aspect of the present invention provides a method for manufacturing the above-mentioned cell sheet construct in vitro, comprising the steps of: culturing vascular endothelial cells on a substrate to form a vascular endothelial cell layer; seeding neural stem cells on the vascular endothelial cell layer to ensure the neural stem cells being physically in direct contact with the vascular endothelial cell layer; and co-culturing the neural stem cells and the vascular endothelial cell layer to differentiate into neurons and branching vasculatures to form a cell sheet construct.

Another aspect of the present invention provides a method for neurovascular reconstruction in vivo, comprising placing the above-mentioned cell sheet construct on a target site where neurovascular reconstruction is required for treating damaged or diseased tissue.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment, and wherein:

FIG. 2A to FIG. 2F show immunocytochemistry of cell samples in Example 4.

FIG. 4A to FIG. 4F show immunocytochemistry of the cell sheet construct of neural stem cells-vascular endothelial cells (NSC-EC) obtained in Example 3.

FIG. 5A to FIG. 5D show immunocytochemistry of the cortical lesion grafted with the cell sheet constructs of neural stem cells-vascular endothelial cells (NSC-EC) of the present invention. FIG. 5A and FIG. 5B show the sample stained with mouse anti-MAP2 antibody (green), rabbit anti-CD31 antibody (red), and DAPI (blue). FIG. 5C and FIG. 5D show the sample stained with rabbit anti-HuN antibody (green), mouse anti-Nestin antibody (red), and DAPI (blue).

FIG. 6A to FIG. 6C show the results of behavioral assessments and body measurements of neurovascular reconstruction in rats with induced traumatic brain injury in Example 7.

DETAILED DESCRIPTION OF THE PREFERRED EMBODIMENT

The present invention provides a cell sheet construct for neurovascular reconstruction. The cell sheet comprises a vascular endothelial cell layer and a neural stem cell layer. The vascular endothelial cell layer has vascular endothelial cells, and the neural stem cell layer has neural stem cells. The vascular endothelial cell layer is directly in contact with the neural stem cell layer, and the two layers directly interact with each other. The vascular endothelial cell layer provides cellular source and extracellular matrix that are needed in differentiation of the neural stem cell layer cells, so that the neural stem cell layer differentiates into neurons, and in return, the vascular endothelial cell layer differentiates into branching vasculatures, which provide nutrient to the neural stem cells.

As used herein, the term "vascular endothelium" refers to the thin layer of simple squamous cells that lines the interior surface of blood vessels. The thin layer of cells form an interface between circulating blood and the rest of the vessel wall. The term "vascular endothelial cells" refers to the cells forming vascular endothelium, including, but not limited to, coronary artery endothelial cells, aortic endothelial cells, cerebral microvascular endothelial cells, umbilical vein endothelial cells, and vascular endothelial cells in dermis. In some embodiments, the vascular endothelial cells are human cerebral microvascular endothelial cells. Vascular endothelial cells used in the present invention are commercially available, for example, but not limited to human coronary arterial endothelial cells (CC-2585, Lonza), human brain microvascular endothelial cells (00194607, Lonza), human aortic endothelial cells (CC-2535, Lonza), human brain microvascular endothelial cells (ACBRI 376, Cell Systems), human umbilical vein endothelial cells (C2519A), and human dermal microvascular endothelial cells (CC-2543).

As used herein, the term "neural stem cells" refers to self-renewing, multipotent cells that generate the main phenotype of the nervous system. Neural stem cells primarily differentiate into neurons, astrocytes, and oligodendrocytes. Neural stem cells include, but are not limited to cerebral neural stem cells, neural crest stem cells, central nervous system stem cells (CNS-SCs), and peripheral neural stem cells. In some embodiments, the neural stem cells are human cerebral neural stem cells. Neural stem cells used in the present invention are commercially available, for example, but not limited to human cortex neural progenitor cell line (SCC007, Millipore), human neural crest stem cell microbeads (130-097-127, Miltenyl Biotec), and human ventral midbrain neural progenitor cell line (SCC008, Millipore).

In some embodiments, the vascular endothelial cell layer further comprises extracellular matrix. The extracellular matrix and the vascular endothelial cells can be used as a carrier for neural stem cell grafting. The extracellular matrix is synthesized and secreted by the vascular endothelial cells and is a collection of marcomolecules distributing between cell surfaces and/or cells. These marcomolecules form a complicate network structure, support and connect tissues, and regulate development of tissues and cellular activities. The extracellular matrix includes polypeptide, collagen, polysaccharide, hyaluronic acid, fibronectin, vitronectin, laminin, and their mixture.

The cell sheet construct of the present invention can further be transferred to a target location and continue differentiating into neurons and branching vasculatures. The target location includes, but is not limited to, neurovascular tissues of limbs, cerebrum, cerebellum, medulla oblongata, spinal cord, heart, lung, liver, stomach, small intestine, large intestine, colon, kidney, gallbladder, pancreas, and uterus. In some embodiments, the target location is cerebral cortex or spinal nerves of a mammal. In some embodiments, the mammal is a rat, mouse, goat, sheep, bison, camel, cow, pig, rabbit, buffalo, horse, or human.

The present invention also provides a novel method for manufacturing the above-mentioned cell sheet construct for neurovascular reconstruction. The formation of the cell sheet construct depends on direct contact and interaction between neural stem cells and vascular endothelial cells. A monolayer of vascular endothelial cells is used as biomaterial in support of cultivating neural stem cells and increase neuronal differentiation of the neural stem cells, and the neural stem cells also facilitate branching morphogenesis of the vascular endothelial cells, so that a cell sheet of neural stem cells-vascular endothelial cells (NSC-EC) functioning as neurovascular tissue is formed.

The method comprises the steps of: culturing vascular endothelial cells on a substrate to form a vascular endothelial cell layer; seeding neural stem cells on the vascular endothelial cell layer to make the neural stem cells be physically in direct contact with the vascular endothelial cell layer; and co-culturing the neural stem cells and the vascular endothelial cell layer to differentiate into neurons and branching vasculatures to form a cell sheet construct.

In some embodiments, the substrate contains collagen, which comprises, but is not limited to type I to type XXVIII collagen. In some embodiments, the collagen is type I collagen.

In some embodiments, the cell density of the vascular endothelial cell layer is about 100,000 cells/cm$^2$ to 300,000 cells/cm$^2$. In some embodiments, the neural stem cells are seeded with a density of about 10,000 cells/cm$^2$ to 100,000 cells/cm$^2$.

In some embodiments, the vascular endothelial cells are cultured in a vascular endothelial cell medium. In some embodiments, the vascular endothelial cell medium is an endothelial cell growth-2 (EGM™-2) medium comprising 1-10% (v/v) fetal bovine serum (FBS), 0.1-5% (v/v) 10,000 U/mL penicillin, and 0.1-5% (v/v) 10,000 U/mL streptomycin.

In some embodiments, the neural stem cells are physically in direct contact with the vascular endothelial cell layer and co-cultured in a neural stem cell/endothelial cell co-culture medium. In some embodiments, the neural stem cell/endothelial cell co-culture medium is serum-free, and by co-culturing the neural stem cells and the vascular endothelial cells, the two types of cells facilitate differentiation of the other type of cells. In some embodiments, the neural stem cell/ endothelial cell co-culture medium contains 50% (v/v) DMEM/F-12 medium and 50% (v/v) EGM™-2 medium and 0.001-0.03% (v/v) human albumin solution, 100-5000 µg/ml transferrin, 0.1-100 µg/ml putrescine DiHCl, 0.1-10 µg/ml insulin, 1-100 ng/ml progesterone 0.1-10 mM L-glutamine, and 1-100 ng/ml sodium selenite.

In some embodiments, the method further comprises transferring the cell sheet construct to a new substrate and keeping culturing the cell sheet construct to increase neuronal differentiation of the neural stem cells and maintain formation of branching vasculatures and differentiation of endothelial cells. In some embodiments, the vascular endothelial cells and the neural stem cells are cultured on a temperature-responsive cell culture surface to form a cell sheet of neural stem cells-vascular endothelial cells (NSC-EC). Then, the cell sheet is detached from the temperature-responsive cell culture surface at room temperature (about 20 to 25° C.), and the detached cell sheet is transferred onto a new substrate through a transfer membrane to keep growing. Neuronal differentiation of the neural stem cells is increased more than 2-fold, and the functions of neurovascular tissue of the cell sheet are improved.

In some embodiments, the new substrate contains collagen, which comprises, but is not limited to type I to type XXVIII collagen. In some embodiments, the collagen is type I collagen.

The present invention also provides a novel method for neurovascular reconstruction in vivo, comprising placing the above-mentioned cell sheet construct on a target site where neurovascular reconstruction is required for treating damaged or diseased tissue.

In some embodiments, the cell sheet construct is transferred from a culture surface to the target site with a transfer membrane.

In some embodiments, the target sites include, but is not limited to, limbs, cerebrum, cerebellum, medulla oblongata, spinal cord, heart, lung, liver, stomach, small intestine, large intestine, colon, kidney, gallbladder, pancreas, and uterus. In some embodiments, the target site is cerebrum or spinal nerves.

As used herein, the singular forms "a", "an", and "the" include plural referents unless the context clearly dictates otherwise. Thus, for example, reference to "a component" includes a plurality of such components and equivalents thereof known to those skilled in the art.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Unless defined otherwise, all technical and scientific terms used herein have the same meaning as commonly understood by a person skilled in the art to which this invention belongs.

The present invention is described in more detail in the following illustrative examples. Although the examples may represent only selected embodiments of the invention, it should be understood that the following examples are illustrative and not limiting.

EXAMPLE 1

Culture of Human Cerebral Neural Stem Cell (hCNSC) Line

The following materials for cell culture are commercially available. Human cerebral neural stem cells (hCNSC) were purchased from Millipore (human cortex neural progenitor cell line, SCC007, Millipore, Mass., USA). Dulbecco's Modified Eagle Medium: Nutrient Mixture F-12, transferrin, putrescine DiHCl, insulin, progesterone, L-glutamine, sodium selenite, 4-hydroxytamoxifen, and Accutase were all purchased from Sigma-Aldrich Corporation (MO, USA). Human albumin solution was purchased from GemBio Laboratory (CA, USA), and human recombinant epidermal growth factor (EGF) and basic fibroblast growth factor (bFGF) were both purchased from PeproTech Inc. (NJ, USA).

Human cerebral neural stem cells (hCNSC) were seeded on culture dishes and maintained in DMEM/F12 medium containing 0.03% human albumin solution, 100 µg/ml transferrin, 16.2 µg/ml putrescine, 5 µg/ml insulin, 60 ng/ml progesterone, 2 mM L-glutamine, 40 ng/ml sodium selenite, 10 ng/ml basic fibroblast growth factor (bFGF), 20 ng/ml epidermal growth factor (EGF), and 100 nM 4-hydroxytamoxifen, at 37° C., 5% $CO_2$ for 48 hours. Then, human cerebral neural stem cells (hCNSC) were detached from the culture dishes by treatment of Accutase, and the hCNSC cell suspension was collected for co-cultur with human cerebral microvascular endothelial cells (hCMEC).

EXAMPLE 2

Culture of Human Cerebral Microvascular Endothelial Cell (hCMEC) Line

The following materials for cell culture are commercially available. Human cerebral microvascular endothelial cells (hCMEC) and EGM™-2 culture medium were purchased from Lonza Biologics (00194607, Lonza, N.J., USA). Fetal bovine serum (FBS) was purchased from PAA Laboratories (ON, Canada). Antibiotics (containing 10,000 U/mL penicillin and 10,000 U/mL streptomycin) were purchased from Invitrogen (CA, USA).

Human cerebral microvascular endothelial cells (hCMEC) were seeded on culture dishes and maintained in EGM™-2 medium containing 5% FBS and 1% antibiotics solution mentioned above, at 37° C., 5% $CO_2$ for 48 hours. After that, human cerebral microvascular endothelial cells (hCMEC) were detached from the culture dishes by treatment of Accutase, and the hCMEC suspension was collected for co-cultur with human cerebral neural stem cells (hCNSC).

EXAMPLE 3

Co-Culture of Human Cerebral Neural Stem Cell (hCNSC) Line and Human Cerebral Microvascular Endothelial Cell (hCMEC) Line Human cerebral microvascular endothelial cell (hCMEC) suspension obtained in Example 2 was seeded on cell culture dishes (BD Biosciences, USA) coated with collagen type I and maintained in EGM™-2 medium containing 5% FBS and 1% antibiotics solution (containing 10,000 U/mL penicillin and 10,000 U/mL streptomycin), at 37° C., 5% $CO_2$ until the cells reached about 200,000 cells/$cm^2$ and formed a vascular endothelial cell layer. After that, human cerebral neural stem cell (hCNSC) suspension obtained in Example 1 was seeded on the vascular endothelial cell layer at a density of about 5,000 cells/$cm^2$, so that the human cerebral neural stem cell (hCNSC) and the human cerebral microvascular endothelial cell (hCMEC) are physically in direct contact and interact with each other. The two types of cells were co-cultured in the neural stem cell/endothelial cell co-culture medium (containing 50% (v/v) DMEM/F-12 medium and 50% (v/v) EGM™-2 medium and 0.015% (v/v) human albumin solution, 500 µg/ml transferrin, 8.1 µg/ml putrescine DiHCl, 2.5 µg/ml insulin, 30 ng/ml progesterone, 1 mM L-glutamine, and 20 ng/ml sodium selenite) at 37° C., 5% $CO_2$ for 7 days. Cell culture medium was replaced every other day until branching vasculatures, neurons and other neural lineage cells were differentiated to form a cell sheet construct of neural stem cells-vascular endothelial cells (NSC-EC). The cell sheet construct was fixed with 4% paraformaldehyde (PFA) for 10 minutes, rinsed with phosphate buffered saline (PBS), and stored in PBS at 4° C. for immunocytochemistry analysis.

In addition, monoculture of human cerebral neural stem cells (hCNSC) (Control group 1), monoculture of human cerebral microvascular endothelial cell (hCMEC) (Control group 2), and co-culture of human cerebral neural stem cells (hCNSC)and human cerebral microvascular endothelial cell (hCMEC) with a Transwell® permeable support (Corning Inc., USA) located between these two types of cells (Control group 3) were used to compare cell differentiation in different treatments.

Monoculture of human cerebral neural stem cells (hCNSC) (Control group 1) was carried out as follows. Human cerebral neural stem cell (hCNSC) suspension obtained in Example 1 was seeded on culture dishes coated with laminin (Sigma-Aldrich Corporation, USA) at a density of about 25,000 cells/$cm^2$ in the neural stem cell/endothelial cell co-culture medium (containing 50% (v/v) DMEM/F-12 medium and 50% (v/v) EGM™-2 medium and 0.015% (v/v) human albumin solution, 500 µg/ml transferrin, 8.1 µg/ml putrescine DiHCl, 2.5 µg/ml insulin, 30 ng/ml progesterone, 1 mM L-glutamine, and 20 ng/ml sodium selenite) at 37° C., 5% $CO_2$. Cell culture medium was replaced every other day. After being cultured for 7 days, the cells were fixed with 4% paraformaldehyde (PFA) for 10 minutes, rinsed with PBS, and stored in PBS at 4° C. for immunocytochemistry analysis.

Monoculture of human cerebral microvascular endothelial cells (hCMEC) (Control group 2) was carried out as follows. Human cerebral microvascular endothelial cell (hCMEC) suspension obtained in Example 2 was seeded on culture dishes coated with collagen type I (BD Biosciences, USA) at a density of about 40,000 cells/$cm^2$ in the neural stem cell/endothelial cell co-culture medium (containing 50% (v/v) DMEM/F-12 medium and 50% (v/v) EGM™-2 medium and 0.015% (v/v) human albumin solution, 500 µg/ml transferrin, 8.1 µg/ml putrescine DiHCl, 2.5 µg/ml insulin, 30 ng/ml progesterone, 1 mM L-glutamine, and 20 ng/ml sodium selenite) at 37° C., 5% $CO_2$. Cell culture medium was replaced every other day. After being cultured for 7 days, the cells were fixed with 4% paraformaldehyde (PFA) for 10 minutes, rinsed with PBS, and stored in PBS at 4° C. for immunocytochemistry analysis.

Co-culture of human cerebral neural stem cells (hCNSC) and human cerebral microvascular endothelial cells (hCMEC) with a Transwell® permeable support (Corning Inc., USA) located between these two types of cells (Control group 3) was carried out as follows. Human cerebral neural stem cell (hCNSC) suspension obtained in Example 1 was seeded into Transwell® permeable supports (with 0.4 µm pore polyester membrane insert, Corning Inc., USA) coated with laminin (Sigma-Aldrich Corporation, USA) at a density of about 15,000 cells/$cm^2$ in DMEM/F12 medium containing 0.03% human albumin solution, 100 µg/ml transferrin, 16.2 µg/ml putrescine, 5 µg/ml insulin, 60 ng/ml progesterone, 2 mM L-glutamine, 40 ng/ml sodium selenite, 10 ng/ml basic fibroblast growth factor (bFGF), 20 ng/ml epidermal growth factor (EGF), and 100 nM 4-hydroxytamoxifen, at 37° C., 5% $CO_2$, for proliferation to 80% confluency. Meanwhile, human cerebral microvascular endothelial cell (hCMEC) suspension obtained in Example 2 was seeded on culture dishes coated with collagen type I (BD Biosciences, USA) at a density of about 40,000 cells/$cm^2$ in EGM-2 medium containing 5% FBS and 1% antibiotics solution (containing 10,000 U/mL penicillin and 10,000 U/mL streptomycin), at 37° C., 5% $CO_2$, for 7 days. The Transwell® permeable supports containing hCNSCs were then transferred to the top of the culture dishes containing hCMECs, and the distance between the transwell membrane and the bottom of the monolayer of hCMECs was about 850 µm. The cells were cultured together in the neural stem cell/endothelial cell co-culture medium (containing 50% (v/v) DMEM/F-12 medium and 50% (v/v) EGM™-2 medium and 0.015% (v/v) human albumin solution, 500 µg/ml transferrin, 8.1 µg/ml putrescine DiHCl 1, 2.5 µg/ml insulin, 30 ng/ml progesterone, 1 mM L-glutamine, and 20 ng/ml sodium selenite) at 37° C., 5% $CO_2$. Cell culture medium was replaced every other day. After being cultured for 7 days, the cells were fixed with 4% paraformaldehyde (PFA) for 10 minutes, rinsed with PBS, and stored in PBS at 4° C. for immunocytochemistry analysis.

The cell sheet construct of neural stem cells-vascular endothelial cells (NSC-EC) obtained in this Example and cell samples of Control groups 1-3 were then analyzed by immunocytochemistry. For immunocytochemistry, cells were blocked with 10% normal goat serum in PBS containing 0.1% Triton X-100 (Sigma) for 30 min prior to incubation with mouse anti-glial fibrillary acid protein (GFAP), which specifically detects neural stem cells and astrocyte (1:3000; Sigma, USA), and rabbit anti-CD31/platelet endothelial cell adhesion molecule 1, which specifically detects endothelial cells representing the "vascular component"(1:200; Abcam, UK), primary antibodies for 18 h at 4° C. After removal of primary antibodies and washing with PBS (3×), cells were incubated with appropriate secondary antibodies (goat anti-mouse Alexa 488-labeled, 1:1000; goat anti-rabbit Alexa 555-labeled, 1:1000, Invitrogen, USA) for 1 h at room temperature (22° C.). Stained coverslips were rinsed in PBS and mounted with Vectashield for fluorescence with diamidino-2-phenylindole (DAPI, Vector Laboratories, USA) to detect cell nuclei. Fluorescence images were captured using a fluorescence microscope (AxioImager M2, Zeiss) to analyze cytoarchitecture, including branching vasculatures and the proportion of neurons and other neural lineage cells differentiated from neural stem cells. The results are shown in FIG. 1A to FIG. 1D.

Figure 1A:
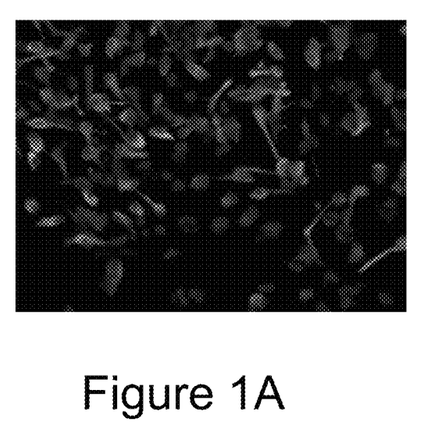
FIG. 1A to FIG. 1D show immunocytochemistry of cell samples in Example 3 stained with mouse anti-GFAP antibody(green), rabbit anti-CD31 antibody (red), and DAPI (blue). The cell sample in FIG. 1A is monoculture of human cerebral neural stem cells (hCNSC) (Control group 1), the cell sample in FIG. 1B is monoculture of human cerebral microvascular endothelial cell (hCMEC) (Control group 2), the cell sample in FIG. 1C is co-culture of human cerebral neural stem cells (hCNSC) and human cerebral microvascular endothelial cells (hCMEC) with a Transwell® permeable support located between these two types of cells (Control group 3), and the cell sample in FIG. 1D is the cell sheet construct of neural stem cells-vascular endothelial cells (NSC-EC) obtained in Example 3.

FIG. 1A shows the immunocytochemistry of monoculture of human cerebral neural stem cells (hCNSC) (Control group 1) stained with mouse anti-GFAP antibody (specifically detects neural stem cells and astrocyte, green), rabbit anti-CD31 antibody (specifically detects endothelial cells, red), and DAPI (detects cell nuclei, blue). As shown in FIG. 1A, there are no vascular endothelial cells in the monoculture of hCNSCs (Control group 1).

Figure 1B:
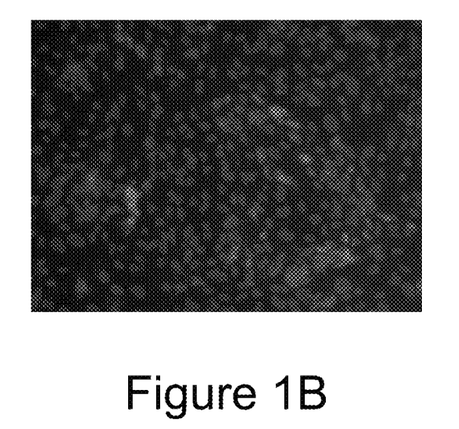

FIG. 1B shows the immunocytochemistry of monoculture of human cerebral microvascular endothelial cell (hCMEC) (Control group 2) stained with mouse anti-GFAP antibody (specifically detects neural stem cells and astrocyte, green), rabbit anti-CD31 antibody (specifically detects endothelial cells, red), and DAPI (detects cell nuclei, blue). As shown in FIG. 1B, there are no neural stem cells or branching vasculatures in the monoculture of hCMECs (Control group 2).

Figure 1C:
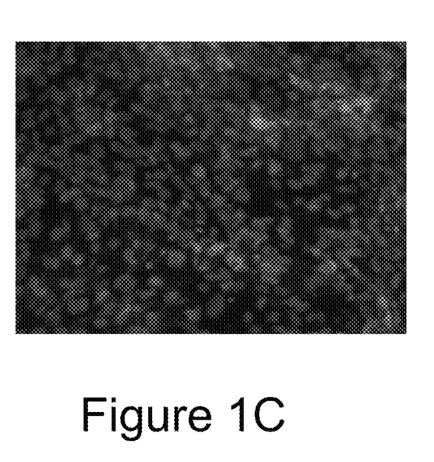

FIG. 1C shows the immunocytochemistry of co-culture of human cerebral neural stem cells (hCNSC) and human cerebral microvascular endothelial cells (hCMEC) with a Transwell® permeable support (Corning Inc., USA) located between these two types of cells (Control group 3) stained with mouse anti-GFAP antibody (specifically detects neural stem cells and astrocyte, green), rabbit anti-CD31 antibody (specifically detects endothelial cells, red), and DAPI (detects cell nuclei, blue). As shown in FIG. 1C, because hCNSCs and hCMECs are not physically in direct contact with each other, there are no differentiated branching vasculatures, neural stem cells, or neural lineage cells in the co-culture (Control group 3).

Figure 1D:
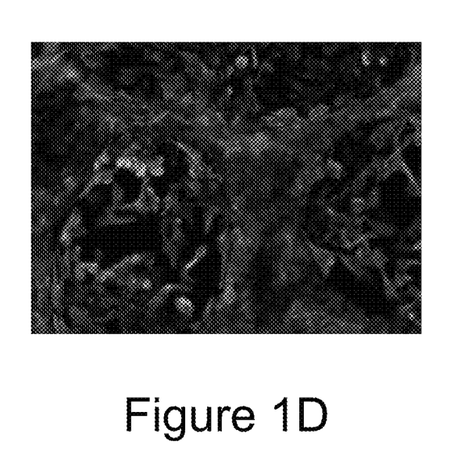

FIG. 1D shows the immunocytochemistry of the cell sheet construct of neural stem cells-vascular endothelial cells (NSC-EC) obtained in this Example stained with mouse anti-GFAP antibody (specifically detects neural stem cells and astrocyte, green), rabbit anti-CD31 antibody (specifically detects endothelial cells, red), and DAPI (detects cell nuclei, blue). As shown in FIG. 1D, the cell sheet construct of neural stem cells-vascular endothelial cells (NSC-EC), which is formed by direct contact and interaction of neural stem cells and vascular endothelial cells, has neural stem cells (stained in green) and branching vasculatures (stained in red, having branched structures).

As the results shown in FIG. 1A to FIG. 1D, neural stem cells and vascular endothelial cells have to be physically in direct contact with each other to form a cell sheet construct of neural stem cells-vascular endothelial cells (NSC-EC) having differentiated neural lineage cells and branching vasculatures.

EXAMPLE 4

Transfer of Cell Sheet Constructs of Neural Stem Cells-Vascular Endothelial Cells (NSC-EC)

The culture dishes with temperature-responsive cell culture surfaces (Nunc® UpCell Surface) used in this Example were purchased from Thermo Scientific (USA). The temperature-responsive cell culture surface is slightly hydrophobic at 37° C., allowing cells to attach and grow. When the temperature of the culture is reduced to below 32° C., the surface becomes very hydrophilic, binds water, swells and releases adherent cells.

Human cerebral microvascular endothelial cell (hCMEC) suspension obtained in Example 2 was seeded on culture dishes with temperature-responsive cell culture surfaces (Nunc® UpCell Surface, Thermo Scientific, USA) in EGM™-2 medium containing 5% FBS and 1% antibiotics solution (containing 10,000 U/mL penicillin and 10,000 U/mL streptomycin), at 37° C., 5% $CO_2$ until the cells reached about 200,000 cells/cm$^2$ and formed a vascular endothelial cell layer. After that, human cerebral neural stem cell (hCNSC) suspension obtained in Example 1 was seeded on the vascular endothelial cell layer at a density of about 5,000 cells/cm$^2$, so that the hCNSCs and the hCMECs are physically in direct contact and interact with each other. The two types of cells were co-cultured in the neural stem cell/endothelial cell co-culture medium (containing 50% (v/v) DMEM/F-12 medium and 50% (v/v) EGM™-2 medium and 0.015% (v/v) human albumin solution, 500 µg/ml transferrin, 8.1 µg/ml putrescine DiHCl, 2.5 µg/ml insulin, 30 ng/ml progesterone, 1 mM L-glutamine, and 20 ng/ml sodium selenite) at 37° C., 5% $CO_2$ for 2 days to form cell sheet constructs of neural stem cells-vascular endothelial cells (NSC-EC). After that, the culture dishes were placed at a 22° C. incubator to make the temperature-responsive cell culture surface hydrophilic, and transfer membranes were covered on the NSC-EC cell sheet construct. About 20 minutes later, the NSC-EC cell sheet constructs detached from the culture dishes and attached to the transfer membranes. The NSC-EC cell sheet constructs were then transferred to glass coverslips which had been coated with collagen at 37° C. for about 30 minutes to allow the NSC-EC cell sheet constructs to attach to the glass coverslips. After the transfer membranes were removed, the NSC-EC cell sheet constructs were cultured in the neural stem cell/endothelial cell co-culture medium (containing 50% (v/v) DMEM/F-12 medium and 50% (v/v) EGM™-2 medium and 0.015% (v/v) human albumin solution, 500 µg/ml transferrin, 8.1 µg/ml putrescine DiHCl, 2.5 µg/ml insulin, 30 ng/ml progesterone, 1 mM L-glutamine, and 20 ng/ml sodium selenite) at 37° C., 5% $CO_2$ for 5 more days. Cell culture medium was replaced every other day. After being cultured for a total of 7 days, the cells were fixed with 4% paraformaldehyde (PFA) for 10 minutes, rinsed with PBS, and stored in PBS at 4° C. for immunocytochemistry analysis.

In addition, monoculture of human cerebral neural stem cells (hCNSC) (Control group 1), monoculture of human cerebral microvascular endothelial cell (hCMEC) (Control group 2), and the cell sheet constructs of neural stem cells-vascular endothelial cells (NSC-EC) without transfer obtained in Example 3 (7-day culture group) were used to compare cell differentiation in different treatments with the cell sheet constructs of neural stem cells-vascular endothelial cells (NSC-EC) with transfer obtained in this Example (Example 4) (2+5-day culture group). Cell culture of Control group 1, Control group 2, and 7-day culture group was described in Example 3.

Immunocytochemistry was described in Example 3, with antibodies of mouse anti-microtubule associate protein-2 (MAP2), which specifically detects neurons (1:500; Abcam, UK), mouse anti-zonula occludens 1 (ZO1), which specifically detects vascular endothelial cells (1:500; Zymed, USA), and rabbit anti-CD31/platelet endothelial cell adhesion molecule 1, which specifically detects endothelial cells representing the "vascular component" (1:200; Abcam, UK). Cell samples were mounted with Vectashield for fluorescence with diamidino-2-phenylindole (DAPI, Vector Laboratories, USA) to detect cell nuclei.

All experiments consisted of 3 biological replicates, each consisting of 3 technical replicates. For each technical replicate, 5 images were taken from different areas on the coverslip prior to calculating a mean value of cell counts for each coverslip. Using SPSS 17 for Mac (IBM, USA), a non-parametric Kruskall-Wallis was used to compare different conditions followed by a Dunn's post-hoc comparison to determine which conditions were significantly different ($p<0.05$). A Mann-Whitney U test was used to compare the markers of differentiation between mono- and co-cultures. Graphs were drawn in Prism 5 (GraphPad, USA) with data points representing the median and bars reflecting the value range.

Figure 2A:
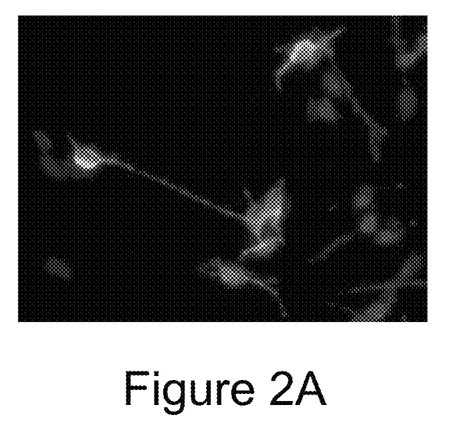
FIG. 2A shows the immunocytochemistry of monoculture of human cerebral neural stem cells (hCNSC) (Control group 1) stained with mouse anti-MAP2 antibody (green) and DAPI (blue).

The results are shown in FIG. 2A to FIG. 2F. FIG. 2A shows the immunocytochemistry of monoculture of human cerebral neural stem cells (hCNSC) (Control group 1) stained with mouse anti-MAP2 antibody (specifically detects neurons, green) and DAPI (detects cell nuclei, blue). As shown in FIG. 2A, there are only few neurons in the monoculture of human cerebral neural stem cells (hCNSC) (Control group 1).

Figure 2B:
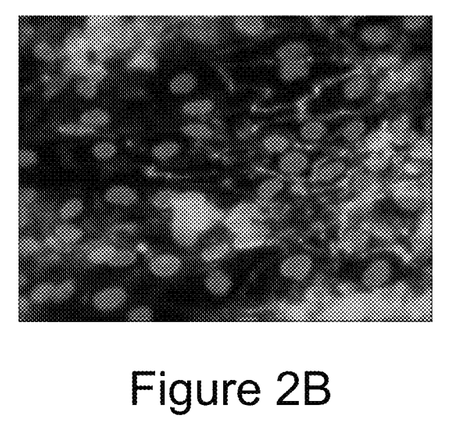
FIG. 2B shows the immunocytochemistry of monoculture of human cerebral microvascular endothelial cell (hCMEC) (Control group 2) stained with mouse anti-ZO1 (green) and DAPI (blue).

FIG. 2B shows the immunocytochemistry of monoculture of human cerebral microvascular endothelial cell (hCMEC) (Control group 2) stained with mouse anti-ZO1 (specifically detects vascular endothelial cells, green) and DAPI (detects cell nuclei, blue). As shown in FIG. 2B, there are no branching vasculatures in the monoculture of hCMECs (Control group 2).

Figure 2C:
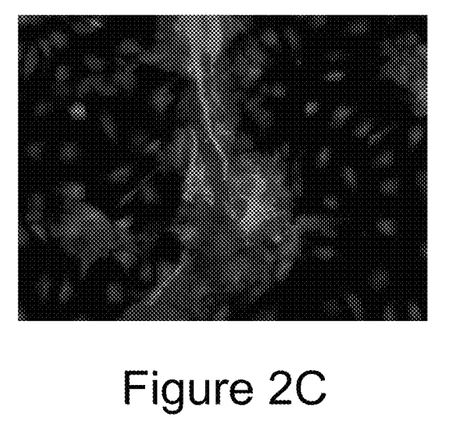
FIG. 2C shows the cell sheet construct of neural stem cells-vascular endothelial cells (NSC-EC) without transfer obtained in Example 3 (7-day culture group) stained with mouse anti-MAP2 antibody (green), rabbit anti-CD31 antibody (red), and DAPI (blue).
Figure 2D:
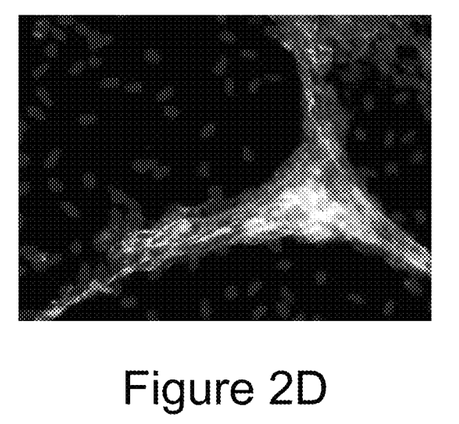
FIG. 2D shows the cell sheet construct of neural stem cells-vascular endothelial cells (NSC-EC) without transfer obtained in Example 3 (7-day culture group) stained with mouse anti-ZO1 (green), rabbit anti-CD31 antibody (red), and DAPI (blue).

FIG. 2C shows the cell sheet constructs of neural stem cells-vascular endothelial cells (NSC-EC) without transfer obtained in Example 3 (7-day culture group) stained with mouse anti-MAP2 antibody (specifically detects neurons, green), rabbit anti-CD31 antibody (specifically detects endothelial cells, red), and DAPI (detects cell nuclei, blue). As shown in FIG. 2C, the NSC-EC cell sheet constructs without transfer obtained in Example 3 (7-day culture group) has differentiated neurons (green) and branching vasculatures (red). FIG. 2D shows the NSC-EC cell sheet constructs without transfer obtained in Example 3 (7-day culture group) stained with mouse anti-ZO1 (specifically detects vascular endothelial cells, green), rabbit anti-CD31 antibody (specifically detects endothelial cells, red), and DAPI (detects cell nuclei, blue). As shown in FIG. 2D, the NSC-EC cell sheet constructs without transfer obtained in Example 3 (7-day culture group) has differentiated branching vasculatures (green and red).

Figure 2E:
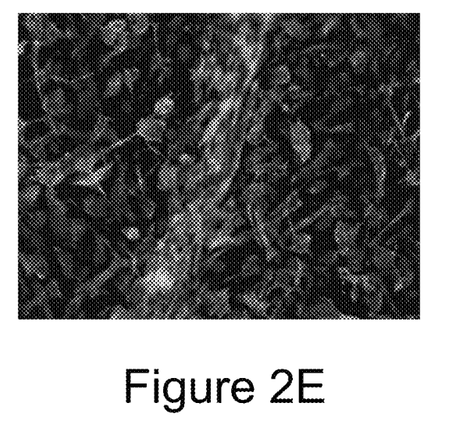
FIG. 2E shows the cell sheet construct of neural stem cells-vascular endothelial cells (NSC-EC) with transfer obtained in Example 4 (2+5-day culture group) stained with mouse anti-MAP2 antibody (green), rabbit anti-CD31 antibody (red), and DAPI (blue).
Figure 2F:
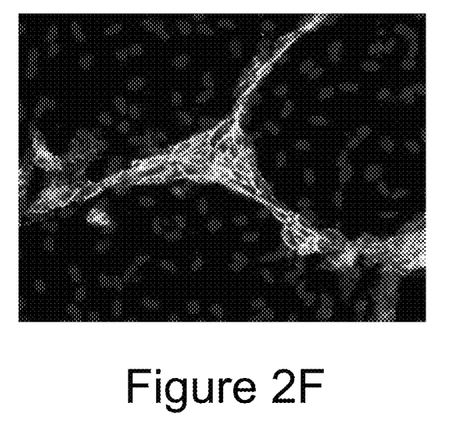
FIG. 2F shows the cell sheet construct of neural stem cells-vascular endothelial cells (NSC-EC) with transfer obtained in Example 4 (2+5-day culture group) stained with mouse anti-ZO1 (green), rabbit anti-CD31 antibody (red), and DAPI (blue).

FIG. 2E shows the cell sheet constructs of neural stem cells-vascular endothelial cells (NSC-EC) with transfer obtained in Example 4 (2+5-day culture group) stained with mouse anti-MAP2 antibody (specifically detects neurons, green), rabbit anti-CD31 antibody (specifically detects endothelial cells, red), and DAPI (detects cell nuclei, blue). As shown in FIG. 2E, the NSC-EC cell sheet constructs with transfer obtained in Example 4 (2+5-day culture group) has differentiated neurons (green) and branching vasculatures (red), and compared to the 7-day culture group, the amount of differentiated neurons (green) in the 2+5-day culture group significantly increased. FIG. 2F shows the NSC-EC cell sheet constructs with transfer obtained in Example 4 (2+5-day culture group) stained with mouse anti-ZO1 (specifically detects vascular endothelial cells, green), rabbit anti-CD31 antibody (specifically detects endothelial cells, red), and DAPI (detects cell nuclei, blue). As shown in FIG. 2F, the NSC-EC cell sheet constructs with transfer obtained in Example 4 (2+5-day culture group) has differentiated branching vasculatures (green and red).

Figure 3:
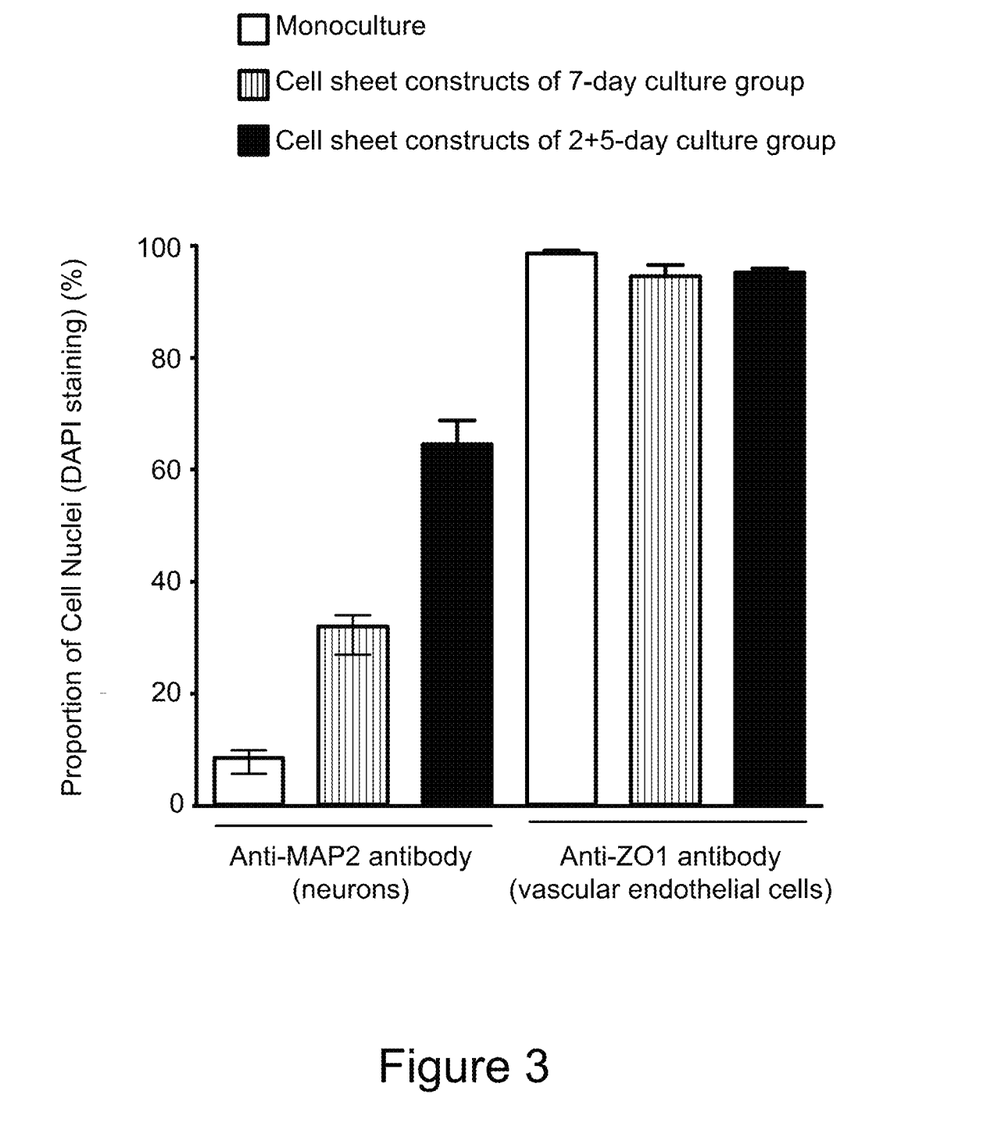
FIG. 3 shows statistical analyses of the immunocytochemistry in Example 4.

FIG. 3 shows statistical analyses of the immunocytochemistry. Neuronal differentiation (MAP2+ cells) of human cerebral neural stem cell (hCNSC) significantly increased from 8% (monoculture of hCNSCs, Control group 1) to 31% (cell sheet constructs of neural stem cells-vascular endothelial cells (NSC-EC) without transfer obtained in Example 3, 7-day culture group) and 64% (NSC-EC cell sheet constructs with transfer obtained in Example 4, 2+5-day culture group), respectively, whereas differentiation of vascular endothelial cells (ZO1+ cells) did not increase significantly. The results show that the NSC-EC cell sheet constructs of the present invention increases neuronal differentiation of neural stem cells.

EXAMPLE 5

Analysis of Extracellular Matrix of the Cell Sheet Constructs of Neural Stem Cells-Vascular Endothelial Cells (NSC-EC) of the Present Invention Extracellular matrix of the cell sheet constructs of neural stem cells-vascular endothelial cells (NSC-EC) obtained in Example 3 was analyzed by immunocytochemistry. Immunocytochemistry was described in Example 3, with antibodies of chicken anti-laminin (1:500, Abcam, USA), mouse anti-fibronectin (1:200, Abcam, USA), sheep anti-hyaluronic acid (1:100, Abcam, USA), mouse anti-vitronectin (1:1000, Abcam, USA), rabbit anti-collagen I (1:500, Abcam, USA), and goat anti-collagen IV (1:200, Millipore, USA). Cell samples were also mounted with Vectashield for fluorescence with diamidino-2-phenylindole (DAPI, Vector Laboratories, USA) to detect cell nuclei. The results are shown in FIG. 4A to 4F.

Figure 4A:
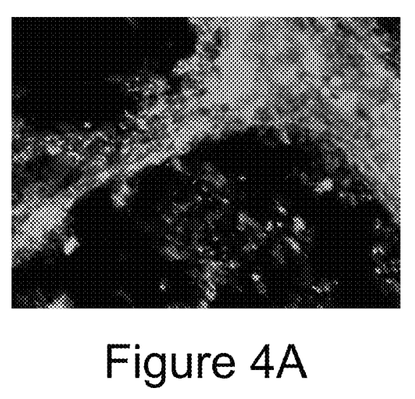
FIG. 4A shows the cell sheet construct stained with chicken anti-laminin antibody (green) and DAPI (blue).

FIG. 4A shows the cell sheet constructs stained with chicken anti-laminin antibody (specifically detects laminin, green) and DAPI (detects cell nuclei, blue). As shown in FIG. 4A, the cell sheet constructs of neural stem cells-vascular endothelial cells (NSC-EC) of the present invention has a great amount of laminin (green).

Figure 4B:
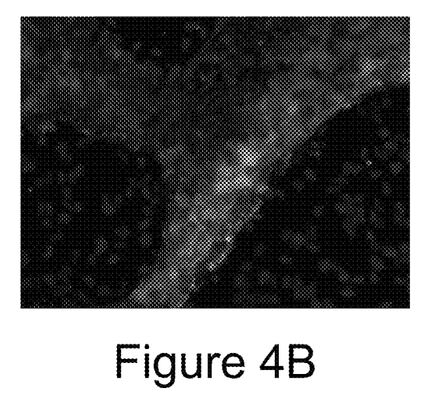
FIG. 4B shows the cell sheet construct stained with mouse anti-fibronectin antibody (green) and DAPI (blue).

FIG. 4B shows the cell sheet constructs stained with mouse anti-fibronectin antibody (specifically detects fibronectin, green) and DAPI (detects cell nuclei, blue). As shown in FIG. 4B, the cell sheet constructs of neural stem cells-vascular endothelial cells (NSC-EC) of the present invention contains fibronectin (green).

Figure 4C:
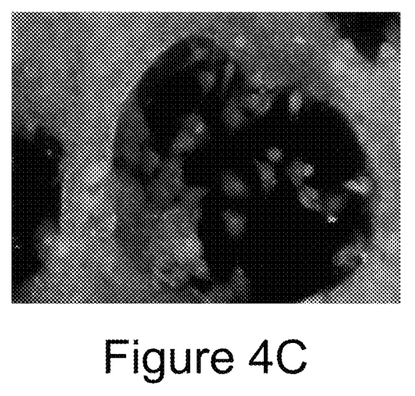
FIG. 4C shows the cell sheet construct stained with sheep anti-hyaluronic acid antibody (green) and DAPI (blue).

FIG. 4C shows the cell sheet constructs stained with sheep anti-hyaluronic acid antibody (specifically detects hyaluronic acid, green) and DAPI (detects cell nuclei, blue). As shown in FIG. 4C, the cell sheet constructs of neural stem cells-vascular endothelial cells (NSC-EC) of the present invention has a great amount of hyaluronic acid (green).

Figure 4D:
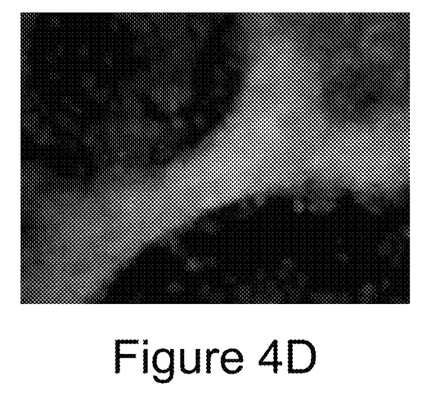
FIG. 4D shows the cell sheet construct stained with mouse anti-vitronectin antibody (green) and DAPI (blue).

FIG. 4D shows the cell sheet constructs stained with mouse anti-vitronectin antibody (specifically detects vitronectin, green) and DAPI (detects cell nuclei, blue). As shown in FIG. 4D, the cell sheet constructs of neural stem cells-vascular endothelial cells (NSC-EC) of the present invention has a great amount of vitronectin (green).

Figure 4E:
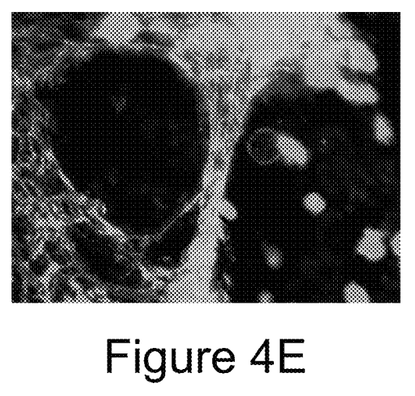
FIG. 4E shows the cell sheet construct stained with rabbit anti-collagen I antibody (green) and DAPI (blue).

FIG. 4E shows the cell sheet constructs stained with rabbit anti-collagen I antibody (specifically detects collagen I, green) and DAPI (detects cell nuclei, blue). As shown in FIG. 4E, the cell sheet constructs of neural stem cells-vascular endothelial cells (NSC-EC) of the present invention has a great amount of collagen I (green).

Figure 4F:
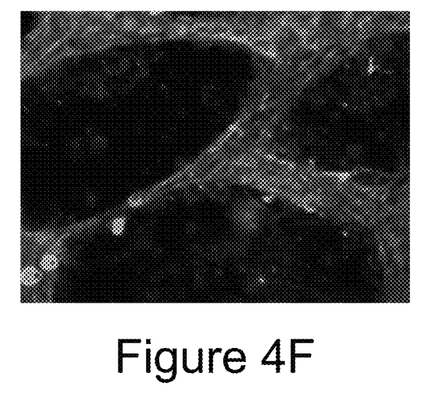
FIG. 4F shows the cell sheet construct stained with goat anti-collagen IV antibody (green) and DAPI (blue).

FIG. 4F shows the cell sheet constructs stained with goat anti-collagen IV antibody (specifically detects collagen IV, green) and DAPI (detects cell nuclei, blue). As shown in FIG. 4F, the cell sheet constructs of neural stem cells-vascular endothelial cells (NSC-EC) contains collagen IV (green).

The results shown in FIG. 4A to FIG. 4F indicate that extracellular matrix of the cell sheet constructs of neural stem cells-vascular endothelial cells (NSC-EC) of the present invention contains at least collagen, hyaluronic acid, fibronectin, vitronectin, and laminin.

EXAMPLE 6

Application of Cell Sheet Constructs of Neural Stem Cells-Vascular Endothelial Cells (NSC-EC) on Neurovascular Reconstruction Adult male Sprague-Dawley (SD) rats weighing 30~350 g were anesthetized with ketamine (75 mg/kg, intraperitoneal injection, i.p.) and xylazine (10 mg/kg, i.p.), supplemented with ketamine (20 mg/kg, i.p.) as needed. Anesthetized rats were then secured in a stereotactic frame, and the scalp was incised along the midline. The right side of the skull was removed (size of craniotomy, about 1 cm$^2$) using a drill and a rongeur. The coordinates of the three points from the bregma were 4 mm rostral/1 mm lateral (coordinate A=+4, +1), 2 mm caudal/1 mm lateral (coordinate B=−2, +1), and 4 mm rostral/6 mm lateral (coordinate C=+4,+6). For the corticectomy, the underlying cortex was sharply cut out with a surgical blade to a depth of 4 mm. Then, the cell sheet constructs of neural stem cells-vascular endothelial cells (NSC-EC) of the present invention (about 1 cm$^2$) was placed onto the cortical lesion with transfer membranes. About 30 minutes later, after the cell sheet constructs detached from the transfer membranes and attached to the surface of the cortical lesion, the transfer membranes were removed, and pia mater, arachnoid mater, and dura mater were sutured. The removed skulls were placed back with bone cement. Seven (7) days later, the rats' brains were fixed with 4% of paraformaldehyde by transcardial perfusion. Cryostat section samples of the fixed brains were then analyzed by immunocytochemistry with mouse anti-MAP2 antibody (specifically detects neurons), rabbit anti-CD31 antibody (specifically detects endothelial cells), mouse anti-Nestin antibody (specifically detects neural stem cells), rabbit anti-HuN antibody (specifically detects human cell nuclei), and DAPI (detects cell nuclei). The results were shown in FIG. 5A to FIG. 5D.

Figure 5A:
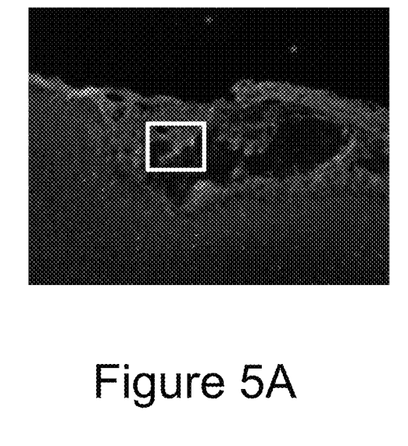
Figure 5B:
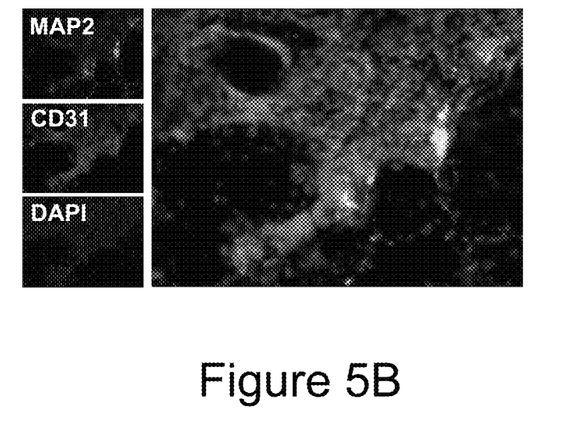
FIG. 5B is an enlarged view within the white box in FIG. 5A.

FIG. 5A and FIG. 5B show the cortical lesion covered with the cell sheet constructs of neural stem cells-vascular endothelial cells (NSC-EC) of the present invention stained with mouse anti-MAP2 antibody (specifically detects neurons, green), rabbit anti-CD31 antibody (specifically detects endothelial cells, red), and DAPI (detects cell nuclei, blue). There are neurons differentiated from neural stem cells (green parts in FIG. 5A and FIG. 5B) and vascular endothelial cells (red parts in FIG. 5A and FIG. 5B) at the location where the cell sheet constructs were implanted.

Figure 5C:
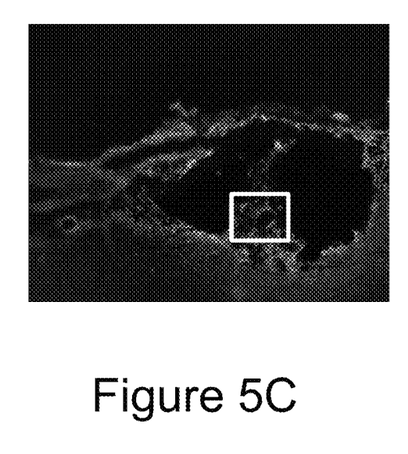
Figure 5D:
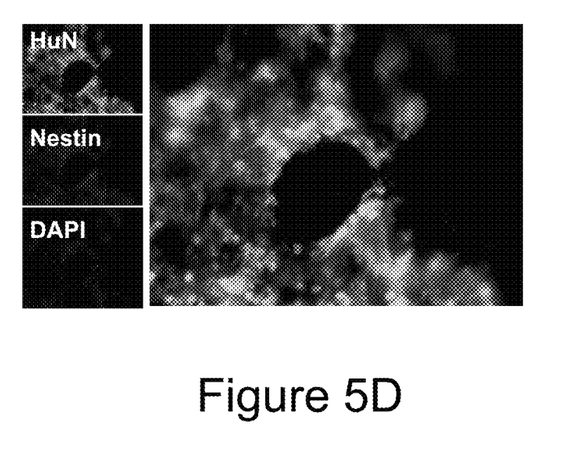
FIG. 5D is an enlarged view within the white box in FIG. 5C.

In addition, FIG. 5C and FIG. 5D show the cortical lesion covered with the cell sheet constructs of neural stem cells-vascular endothelial cells (NSC-EC) of the present invention stained with rabbit anti-HuN antibody (specifically detects human cell nuclei, green), mouse anti-Nestin antibody (specifically detects neural stem cells, red), and DAPI (detects cell nuclei, blue). As shown in FIG. 5C and FIG. 5D, human cells (green parts) grew in the cortical lesion of rat brains, indicating that the neurons differentiated from neural stem cells as well as the vascular endothelial cells in FIG. 5A and FIG. 5B came from the NSC-EC cell sheet constructs of the present invention.

As indicated in FIG. 5A to FIG. 5D, the cell sheet constructs of neural stem cells-vascular endothelial cells (NSC-EC) of the present invention can be used in transplantion surgery and reconstruct neurovascular tissues at lesion sites.

EXAMPLE 7

Evaluation of Neurovascular Reconstruction in Induced Traumatic Brain Injury with Cell Sheet Constructs of Neural Stem Cells-Vascular Endothelial Cells (NSC-EC)

Adult male Sprague-Dawley (SD) rats weighing 30~350 g were anesthetized with ketamine (75 mg/kg, intraperitoneal injection, i.p.) and xylazine (10 mg/kg, i.p.), supplemented with ketamine (20 mg/kg, i.p.) as needed. Anesthetized rats were then secured in a stereotactic frame, and the scalp was incised along the midline. The right side of the skull was removed (size of craniotomy, about 1 cm$^2$) using a drill and a rongeur. The coordinates of the three points from the bregma were 4 mm rostral/1 mm lateral (coordinate A=+4, +1), 2 mm caudal/1 mm lateral (coordinate B=−2, +1), and 4 mm rostral/6 mm lateral (coordinate C=+4, +6). For the corticectomy, the underlying cortex was sharply cut out with a surgical blade to a depth of 4 mm. (1) In the brain injury group (Control group), after a craniotomy and exposure of a triangular window displaying the underlying right frontoparietal area of the brain covered by the dura, the dura was carefully incised with a number 20 needle to minimize bleeding, before cutting of the underlying cortex as described above; (2) In the brain injury with NSC/EC cell sheet group (Treatment group), after the procedure for the control groups was carried out, a piece of cell sheet of NSC/EC, with an area of about 1 cm$^2$, was placed onto the lesion cavity formed 20 minutes after tissue removal from the frontoparietal area. For ensuring the attachment of the cell layer on the brain tissue, duration of 1 to 30 minutes of placement of the sheet was required before removing the UpCell™ transfer membrane (Thermo Scientific, NH, USA).

Modified Neurologic Severity Score (mNSS) was performed 1, 3, 7, 14, 21 and 28 days after corticectomy by individuals blinded to the experimental groups. mNSS consists of motor, sensory, balance, and reflex tests. Neurologic function is graded on a scale of 0-18 (normal score 0; maximal deficit score 18, Table 1). One score point indicates the inability to perform the test or the lack of a reflex; thus, the higher score, the more severe injury.

TABLE 1

Neurological severity score

| Modified neurological severity scores (mNSS)[a] | Points |
|---|---|
| Motor test | 6 |
| Raising the rat by the tail | |
| 1 Flexion of forelimb | |
| 1 Flexion of hind limb | |
| 1 Head moved more than 10° to the vertical axis within 30 s | |
| Walking on the floor (normal = 0; maximum = 3) | |
| 0 Normal walk | |
| 1 Inability to walk straight | |
| 2 Circling toward the paretic side | |
| 3 Falling down to the paretic side | |
| Sensory tests | 2 |
| 1 Placing test (visual and tactile test) | |
| 2 Proprioceptive test (deep sensation, pushing the paw against the table edge to stimulate limb muscles) | |
| Beam balance test (normal = 0; maximum = 6) | 6 |
| 0 Balances with steady posture | |
| 1 Grasps side of beam | |
| 2 Hugs the beam and one limb falls down from the beam | |
| 3 Hugs the beam and two limb falls down from the beam, or spins on beam (>60 s) | |
| 4 Attempts to balance on the beam but falls off (>40 s) | |
| 5 Attempts to balance on the beam but falls off (>20 s) | |
| 6 Falls off: no attempts to balance or hang on to the beam (<20 s) | |
| Reflexes absent and abnormal movements | 4 |
| 1 Pinna reflex (head shake when the auditory meatus is touched) | |
| 1 Corneal reflex (eye blink when the cornea is lightly touched with cotton) | |
| 1 Startle reflex (motor response to a brief noise from snapping a clipboard and paper) | |
| 1 Seizures, myoclonus, myodystony | |
| Maximum points | 18 |

[a]One point is awarded for the inability to perform a task or for the lack of a tested reflex. A score of 13-18 indicates severe injury; 7-12, moderate injury; 1-6, mild injury.

The contralateral body swing test was used to assess bias in swing direction in rats elevated by the base of the tail. Twenty separate tests were performed with the number of right and left initial head/torso turns recorded. Prior to surgically induced brain injury, rats swing right and left with near equal frequency, leading to a contralateral ratio of 50%. Following corticectomy, rats with cortical lesions have a biased swing to the side contralateral to the injury with a bias approaching 100%. The contralateral swing test was performed 1, 3, 7, 14, 21 and 28 days after corticectomy by individuals blinded to the experimental groups.

In addition, each mouse was weighed 1, 3, 7, 14, 21 and 28 days after brain injury.

Figure 6A:
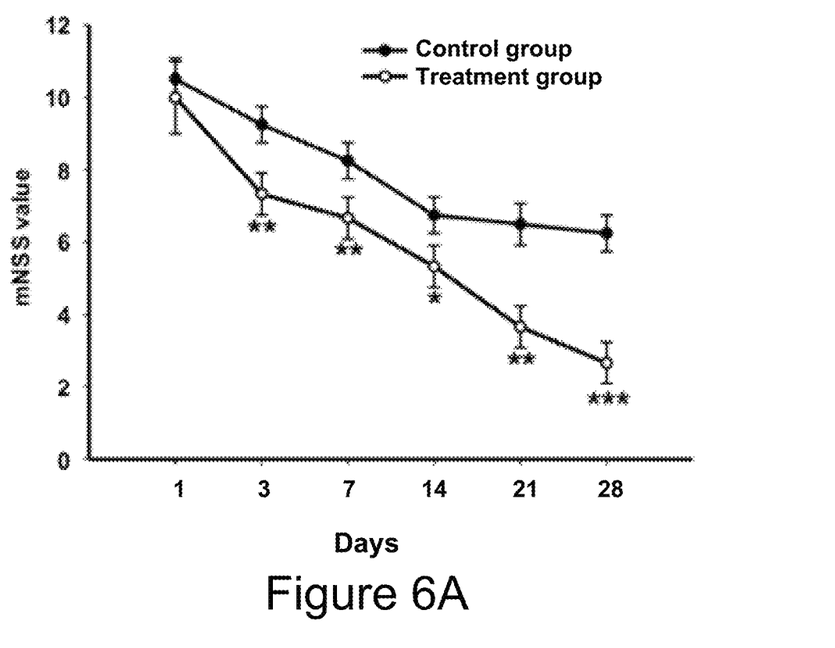
FIG. 6A shows the modified neurological severity score (mNSS) of the rats.
Figure 6B:
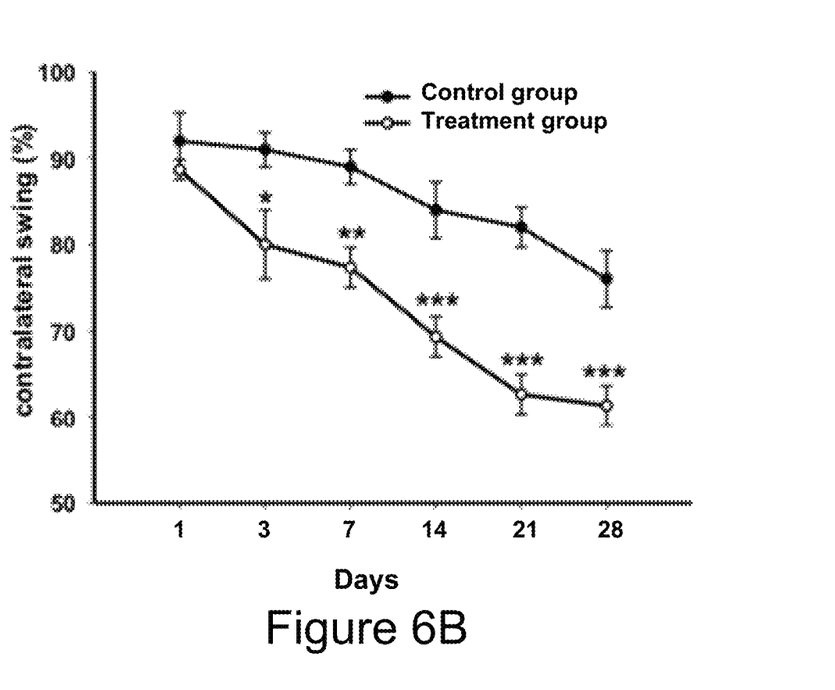
FIG. 6B shows the results of contralateral swing test.
Figure 6C:
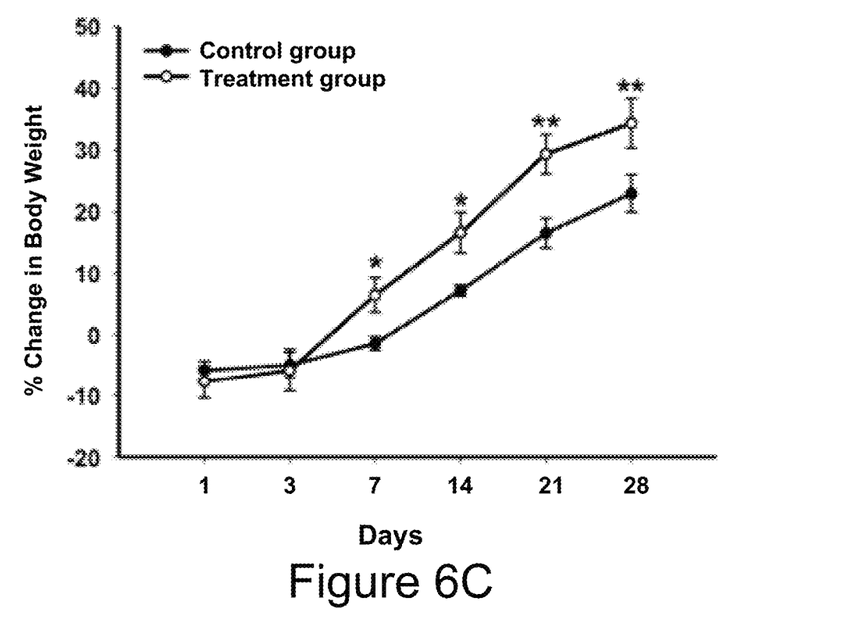
FIG. 6C shows the average body weight of the rats after brain injury and treatment.

The results are shown in FIG. 6A to FIG. 6C. FIG. 6A shows the mNSS of the rats. As shown in FIG. 6A, mNSS of the rats in the Treatment group was statistically lower than the Control group from Day 3. It indicates that neurological recovery in rats treated with cell sheet transplantation was greater than the rats in the control group.

FIG. 6B shows the results of contralateral swing test. As shown in FIG. 6B, improvement in the contralateral swing test for rats in the Treatment group was statistically greater than the Control group from Day 3. The rats treated with cell sheet transplantation had an improved contralateral ratio of 61%, in contrast with a ratio of 78% in the Control group.

FIG. 6C shows the average body weight of the rats after brain injury. As shown in FIG. 6C, body weight of the rats in the Treatment group increased gradually and was higher than the weight before corticectomy on postoperative day 7 (Day 7). In contrast, rats in the Control group did not regain body weight until Day 14. Body weight of the rats in the Treatment group was statistically higher than Control group from Day 7.

EXAMPLE 8

Evaluation of Neurovascular Reconstruction in Induced Traumatic Spinal Injury with Cell Sheet Constructs of Neural Stem Cells-Vascular Endothelial Cells (NSC-EC)

Adult male C57BL/6J mice weighing 25-30 g were used in this study. The mice were anesthetized with sodium pentobarbital (80 mg/kg, i.p.), and the hairs on their back were clipped. A midline incision above the lumbar spine exposed the left sixth lumbar transverse process. The transverse process was removed carefully with a small scraper. The underlying fifth lumbar (L5) nerve root was isolated and then tightly ligated with 8-0 nylon thread. Next, the wound was closed with 2-3 muscle sutures (3-0 absorbable nylon suture) and 4-5 skin sutures (3-0 non-absorbable nylon suture).

A 14-day schedule was used in this study. In the spinal nerve ligation (SNL) with NSC/EC cell sheet group (Treatment group), 20 minutes after the procedure for the control group was carried out, a piece of cell sheet of NSC/EC, with an area of about 1 $cm^2$, was placed surrounding the segment of ligated spinal nerve (L5). For ensuring the attachment of the cell layer on the nerve, duration of 1 to 30 minutes of placement of the sheet was required before removing the UpCell™ transfer membrane (Thermo Scientific, NH, USA). Von Frey tests were performed prior and 3, 5, 7, 10, and 13 days after SNL by individuals blinded to the experimental groups. After the last Von Frey test on day 13, the animals were sacrificed on day 14 for immunohistochemistry study. The number of animals in each group was at least 8 at the beginning of the experiment; and at least 5 mice in each group survived to complete this study.

Von Frey test for determination of mechanical allodynia is described as follows. The mice were individually placed in a transparent acrylic box (9×9×15 cm) with a wire-mesh bottom and allowed to acclimate to their environment for at least 30 min. The mechanical stimulus was applied from underneath to the plantar aspect of the hind limb, with a gradual increase in pressure by means of an Electronic von Frey apparatus (IITC Inc., CA, USA). The end point was characterized by the removal of the paw followed by clear flinching movements. After the paw withdrawal, the intensity of the pressure was automatically recorded. Each test was repeated 3 times with intervals of 5 minutes, and the average value was used.

The data were expressed as means±S.E.M. Student's t test and one-way ANOVA were used to analyze the data. A difference was considered to be significant at $p<0.05$.

Figure 7:
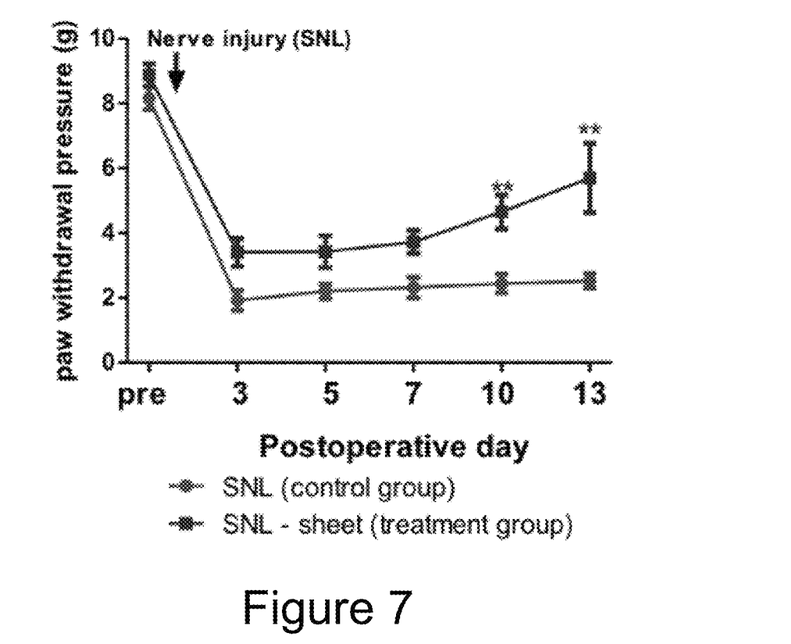
FIG. 7 shows the results of Von Frey test for mice receiving spinal nerve ligation and grafting of the neural stem cell-vascular endothelial cell (NSC-EC) sheet in Example 8.

The results of Von Frey test are shown in FIG. 7. The results of Von Frey test for the control group and treatment group indicate that the improvement of paw withdrawal pressure in the group of NSC/EC sheet treatment was statistically greater than the control group from day 10 after the surgery.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments are chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A method for manufacturing a cell sheet constructfor neurovascular reconstruction, consisting of:
    step 1: culturing vascular endothelial cells on a cell culture dish with a vascular endothelial cell medium to form a vascular endothelial cell layer;
    step 2: seeding neural stem cells on the vascular endothelial cell layer to ensure the neural stem cells being physically in direct contact with the vascular endothelial cell layer;
    step 3: co-culturing the neural stem cells and the vascular endothelial cell layer to form a cell sheet construct of neural stem cells-vascular endothelial cells (NSC-EC);
    step 4: detaching the cell sheet construct of NSC-EC from the culture dish and transferring the same to a cell culture surface; and
    step 5: culturing the cell sheet construct of NSC-EC obtained from step 4 with an NSC-EC co-culture medium to provide a cell sheet construct for neurovascular reconstruction.

2. The method of claim 1, wherein the neural stem cells are human cerebral neural stem cell line, SCC007, Millipore, Merck.

3. The method of claim 1, wherein in step 1, the cell culture dish has a temperature-responsive cell culture surface.

4. The method of claim 1, wherein in step 1, the cell density of the vascular endothelial cell layer is 100,000 cells/cm$^2$ to 300,000 cells/cm$^2$.

5. The method of claim 1, wherein in step 2, the neural stem cells are seeded with a density of 10,000 cells/cm$^2$ to 100,000 cells/cm$^2$.

6. The method of claim 1, wherein the vascular endothelial cell medium is an endothelial cell growth-2 (EGM™-2, Lonza) medium comprising 1-10% (v/v) fetal bovine serum (FBS), 0.1-5% (v/v) 10,000 U/mL penicillin and 0.1-5% (v/v) 10,000 μg/mL streptomycin.

7. The method of claim 1, wherein in step 3, the neural stem cells and the endothelial cell layer are co-cultured in a neural stem cell/endothelial cell co-culture medium.

8. The method of claim 7, wherein the neural stem cell/endothelial cell co-culture medium comprises 50% (v/v) DMEM/F-12 medium and 50% (v/v) EGM™-2 medium and 0.001-0.03% (v/v) human albumin solution, 100-5000 μg/ml transferrin, 0.1-100 μg/ml putrescine DiHCl, 0.1-10 μg/ml insulin, 1-100 ng/ml progesterone, 0.1-10 mM L-glutamine, and 1-100 ng/ml sodium selenite.

* * * * *